US009096516B2

(12) United States Patent
Sugiura et al.

(10) Patent No.: US 9,096,516 B2
(45) Date of Patent: Aug. 4, 2015

(54) PRODUCTION METHOD OF N-VINYL-2-PYRROLIDONE

(75) Inventors: Hideto Sugiura, Kawasaki (JP); Toru Inaoka, Yokohama (JP); Shigeyuki Nozaki, Yokohama (JP); Yoshihisa Oka, Chigasaki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 13/109,450

(22) Filed: May 17, 2011

(65) Prior Publication Data

US 2011/0218344 A1 Sep. 8, 2011

Related U.S. Application Data

(63) Continuation of application No. 11/918,228, filed as application No. PCT/JP2006/307892 on Apr. 7, 2006.

(30) Foreign Application Priority Data

Apr. 11, 2005 (JP) ................. 2005-113523
Jul. 28, 2005 (JP) ................. 2005-218778

(51) Int. Cl.
*C07D 201/16* (2006.01)
*B01D 9/00* (2006.01)
*C07D 207/267* (2006.01)

(52) U.S. Cl.
CPC .......... *C07D 207/267* (2013.01); *B01D 9/0059* (2013.01); *C07D 201/16* (2013.01)

(58) Field of Classification Search
CPC ............................ C07D 201/16; B01D 9/0059
USPC ....................................................... 548/555
See application file for complete search history.

(56) References Cited

U.S. PATENT DOCUMENTS

| | | | | |
|---|---|---|---|---|
| 5,039,817 A * | 8/1991 | Kroker et al. | ................. | 548/543 |
| 5,329,021 A * | 7/1994 | Cohen et al. | ................. | 548/543 |
| 5,710,284 A | 1/1998 | Schmidt-Radde et al. | | |
| 6,436,243 B1 | 8/2002 | Yamaguchi et al. | | |
| 6,703,511 B2 | 3/2004 | Eck et al. | | |
| 7,138,528 B2 * | 11/2006 | Gupta et al. | ................. | 548/555 |
| 2003/0166947 A1 | 9/2003 | Eck et al. | | |
| 2003/0176712 A1 | 9/2003 | Abe et al. | | |
| 2004/0133015 A1 | 7/2004 | Hammon et al. | | |
| 2006/0281928 A1 | 12/2006 | Sugiura et al. | | |

FOREIGN PATENT DOCUMENTS

| | | |
|---|---|---|
| DE | 195 36 859 A1 | 4/1997 |
| JP | 8-506580 A | 7/1996 |
| JP | 9-169724 A | 6/1997 |
| JP | 2001-122854 A | 5/2001 |
| JP | 2003-238532 A | 8/2003 |
| JP | 2003-534322 A | 11/2003 |
| JP | 2004-528371 A | 9/2004 |
| JP | 2004-345993 A | 12/2004 |
| JP | 2004-345994 A | 12/2004 |
| WO | WO 89/03823 A1 | 5/1989 |
| WO | WO 2004/103965 A1 | 12/2004 |

OTHER PUBLICATIONS

Myerson (Handbook of Industrial Crystallization, 2nd ed. (2002), 313 pages).*
Mullin (Crystallization, 4th ed (2001), 594 pages).*
"Understanding Chemistry for Advanced Level" Ted Lister, Janet Renshaw; Publisher: Nelson Thornes, Nov. 19, 1999, 680 pages. p. 579 provided.*
Extended European Search Report from European Patent Office issued in corresponding European Patent Application No. 10016226.2 dated Apr. 26, 2011.
PCT/ISA/210 dated Jun. 27, 2006.
PCT/ISA/237 dated Jun. 27, 2006.
An Official Action issued on Sep. 18, 2009, in corresponding Chinese Patent Application No. 2006800118100, and an English translation thereof.
Supplementary Search Report dated Oct. 28, 2009 issued in European Patent Application No. EP 06 73 1828.
Masakuni Matsuoka, "Purification of Organic Crystals by Sweating and Column Crystallizer," Fac. Technol., Tokyo Univ. Agric. Technol., Koganei, 184, Japan, Kagaku Sochi (1988), 30(10), 41-7, Database CA [Online], XP002550771 retrieved from STN Database Accession No. 1989:40999, Chemical Abstracts Service, Columbus, Ohio.
Office Action issued by the European Patent Office issued in corresponding European Patent Application No. 10 016 226.2 dated Nov. 3, 2011.
Myerson, "Handbook of Industrial Crystallization," $2^{nd}$ Ed. (2002), 313 pages.
Mullin, "Crystallization," $4^{th}$ Ed. (2001), 594 pages, Chapters 7-10 provided.

* cited by examiner

*Primary Examiner* — Robert Havlin
(74) *Attorney, Agent, or Firm* — Buchanan Ingersoll & Rooney PC

(57) ABSTRACT

A method for producing N-vinyl-2-pyrrolidone by crystallization including: controlling a water content in a feed N-vinyl-2-pyrrolidone solution at an inlet of a crystallizer so as to be not lower than 0.7% by weight and not higher than 10% by weight based on the total weight of the N-vinyl-2-pyrrolidone solution; and supplying the feed N-vinyl-2-pyrrolidone solution to a crystallization process.

11 Claims, 1 Drawing Sheet

PRODUCTION METHOD OF N-VINYL-2-PYRROLIDONE

CROSS REFERENCE TO RELATED APPLICATIONS

This application is a continuation of application Ser. No. 11/918,228, filed Oct. 11, 2007, which is a §371 of PCT/JP2006/307892, filed Apr. 7, 2006, which in turn claims priority to Japanese Application No. 2005-113523, filed Apr. 11, 2005 and Japanese Application No. 2005-218778, filed Jul. 28, 2005, the disclosures of all of which are incorporated herein by reference in their entireties.

TECHNICAL FIELD

The present invention relates to a stable production method of high-purity N-vinyl-2-pyrrolidone.

BACKGROUND ART

N-vinyl-2-pyrrolidone (hereinafter, abbreviated as "NVP") is useful as an reactive diluent, and polymers of NVP are used extensively in various fields such as pharmaceuticals, cosmetics, adhesives, paints, dispersants, inks, electronic parts and photoresist materials because of their advantages such as biocompatibility, stability and hydrophilicity.

Impurities are firmly required to be removed in these fields. Therefore, it is proposed to control the concentration of impurities in a mother liquor at a constant level in search of a method for obtaining high-purity NVP (JP-A-2004-345994).

A method for obtaining NVP of extremely high purity while improving energy efficiency by reducing stages in a crystallization process is proposed (JP-A-2004-345993).

SUMMARY

In JP-A-2004-345994 and JP-A-2004-345993, the purity of NVP to be supplied to the first crystallization process is generally low, resulting in low purity of the obtained NVP and a high load of a crystal purification process, because a mother liquor from the first crystallization process is recycled for use to the first crystallization process. Further, much time is necessary in a purification process to obtain high-purity NVP, which sometimes results in low production efficiency.

We have found, after having intensively studied a way to solve the above problems, that high-purity NVP is obtained from the first crystallization process and also the production efficiency is improved by supplying the mother liquor from the first crystallization process to the second crystallization process.

The present invention can provide a production method of NVP characterized by comprising at least two crystallization processes, supplying the mother liquor from the first crystallization process to second crystallization process and supplying, as needed, the crystals from the crystallization processes to a crystal purification process where a sweating phenomenon is applied.

JP-A-2004-345994 discloses that it is preferable to control the concentration of impurities in a crude NVP solution at a constant level at the inlet of a crystallizer to prevent quality degradation of obtained NVP, but does not give any detail information on controlling the concentration of impurities.

It has been found that under some concentration of impurities, crystals deposit on the heat transfer surface of a crystallizer to cause plugging and thus suspend an operation, impairing stable production of NVP.

We took notice of a water content and found that high-purity NVP can be stably produced without suspending an operation by controlling the water content in a feed NVP solution within a specific range.

According to the present invention, high-purity NVP can be stably produced without plugging in a crystallizer caused by crystals that could deposit on the heat transfer surface by controlling the water content in a feed NVP solution within a specific range.

BEST MODE FOR CARRYING OUT THE INVENTION

Each embodiment of the present invention will be described in detail hereinafter.

In the first embodiment of the present invention, a production method of NVP can be provided, characterized by comprising at least two crystallization processes, supplying the mother liquor from the first crystallization process to the second crystallization process and supplying, as needed, the crystals from the crystallization process to a crystal purification process where a sweating phenomenon is applied.

The present invention will be described in more detail based on the attached drawings.

Figure 1:
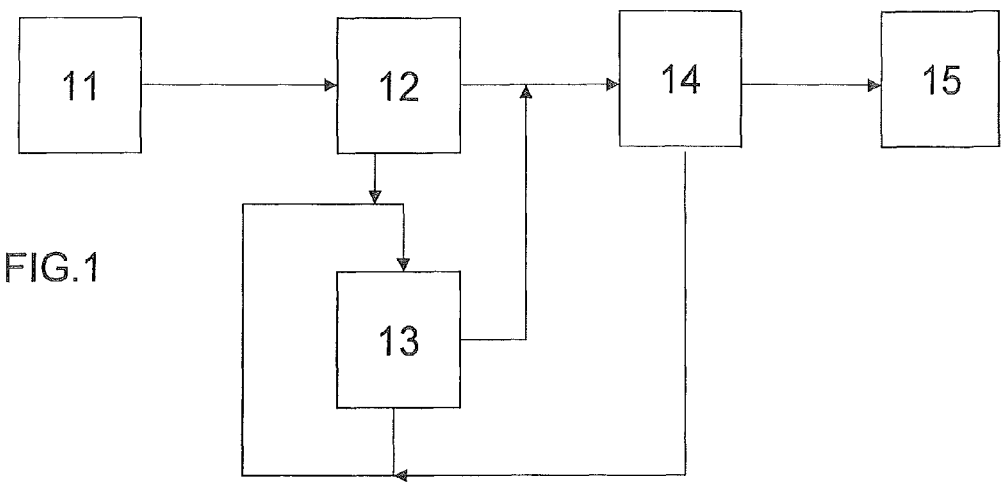
FIG. 1 is an illustration showing a method for purifying NVP in crystallization.

FIG. 1 is an illustration showing a method for purifying NVP in crystallization.

In FIG. 1, purification of NVP is carried out in a combination of two crystallizers 12, 13 and crystal purification apparatus 14. The first crystallization process is supplied with only distilled NVP 11, whereas the second crystallization process is supplied with a recovered mother liquor.

Distilled NVP is used as feed NVP to the first crystallization process using crystallizer 12, whereas a mother liquor from the first crystallization process and a mother liquor from the second crystallization process and, as needed, a mother liquor and a sweating solution from the crystal purification process using crystal purification apparatus 14 are mixed and controlled for water content thereof to obtain a feed solution to the second crystallization process using crystallizer 13. The feed NVP is crystallized in the first crystallization process and the crude crystals obtained by filtration are purified in the crystal purification process to obtain product 15. The crude crystals obtained from the second crystallization process are sent to the crystal purification process and purified in the same way to obtain product 15.

Distilled NVP provides crystals of higher purity because it contains less amount of impurities compared with a recovered mother liquor. Therefore, the crystals to be supplied to a crystal purification process of which the purity is higher than that of the crystals obtained from the recovered mother liquor improve the purity of the product NVP. Further, this leads to an increase of the amount of production due to a lighter load in the crystal purification process.

In this method, part of a mother liquor and a sweating solution recovered from a crystal purification process is removed to adjust the concentration of impurities. The concentration of impurities in the mother liquor is controlled so as to be generally not higher than 10%, preferably not higher than 6%.

The first crystallization process, the second crystallization process and the crystal purification process in the first embodiment can be operated continuously. Each process may be operated independently, but preferably operated continuously in view of production efficiency.

Next, each process in the first embodiment will be described in order.

(i) Feed NVP to be Supplied at the Inlet of a Crystallizer

Feed NVP to be supplied in the first embodiment includes crude NVP synthesized by various methods such as crude NVP obtained by vinylating 2-pirrolidone with acetylene; crude NVP obtained as a dehydrated salt by reacting butyrolactone with ethanolamine and then replacing a hydroxyl group of thus obtained 1-(β-oxyethyl)-2-pirrolidone with chlorine using thionyl chloride; crude NVP obtained by removing an acetic acid from an acetic ester intermediate produced by reacting N-(2-hydroxyethyl)-2-pirrolidone with acetic anhydride; and crude NVP obtained by gas-phase intramolecular dehydration (sometimes abbreviated as "gas-phase dehydration") of N-hydroxyethyl-2-pirrolidone in the presence of a catalyst.

The melting point of NVP is 13.5° C.

Crude NVP that contains few impurities may be used directly as a raw material for crystallization, but when it contains many impurities, it is used as a raw material for crystallization after purified by a known method such as fractional distillation. The impurities include water, 2-pirrolidone that is a decomposition product of N-hydroxyethyl-2-pirrolidone, N-hydroxyethyl-2-pirrolidone that is an unreacted raw material, and a polymer.

Generally, distilled NVP can be used as a raw material for crystallization. Because impurities removed by distillation and impurities removed by crystallization are not always the same, the combination of both methods is effective for improving purity. The purity of NVP is not particularly restricted, but it is preferably within the range between about 97% and about 99%. Even when NVP has a purity of over 99.95%, it can be used as a raw material without any problem if its purity is lower than that of the product NVP.

NVP can be distilled by a known method. For example, see JP-A-2004-345994.

A NVP-containing solution recovered from a crystallization process, a filtration process, a crystal purification process and the like may be used as a part of raw material for crystallization. The mixing thereof is carried out using a known agitator. The mixing ratio with distillated NVP is adjusted as appropriate without particular restriction.

(ii) Crystallization Process

The method for crystallization is not restricted, so long as crystals can be obtained by supercooling a liquid NVP. Crystallization itself can employ a known apparatus and method. A crystallization apparatus includes, for example, a continuous crystallizer such as a forced-circulation type crystallizer, a multistage crystallizer, a conveying layer type crystallizer, a classified-product-removal crystallizer, a turbulent type mixed—and classified-product-removal crystallizer, a double crystallizer, a direct-contact-refrigeration crystallizer and a flocculate formation technology; and a cooling type crystallizer such as a tank type crystallizer, a Swenson-Walker crystallizer, a Howard crystallizer and a drum flaker.

A feed NVP solution is crystallized in the above crystallizers making use of a cooling medium such as water and an aqueous solution of ethylene glycol. Crystallization is preferably carried out continuously by controlling the temperature (for example, −20° C. to 13.5° C.) of the mother liquor discharged from the outlet so that the concentration of the slurry (mother liquor containing depositing crystals) in the mother liquor is a specified concentration, for example, 5 to 60%, and adjusting a retention time. The above mother liquor (feed NVP in a crystallizer) can be recycled to the crystallization process.

In the above crystallization operation, a stabilizer may be added to a feed NVP solution and a mother liquor. The stabilizer is not restricted so long as it can inhibit NVP polymerization, and includes, for example, a phenol-based antioxidant and an amine-based polymerization inhibitor. These stabilizers may be used alone or in combination. Among others, N,N'-di-sec-butyl-p-phenylenediamine, p-phenylenediamine, N, N'-diethyl-p-phenylenediamine, N, N'-diphenyl-p-phenylenediamine or 2,6-t-butyl-4-hydroxytoluene are preferable in view of inhibiting ability against NVP polymerization. The amount of a stabilizer to be used is not particularly restricted so long as NVP polymerization is inhibited or reduced. A stabilizer is present in the concentration range of generally not higher than 1.5% by weight (not including 0%), preferably 0.1 ppm to 1.0% by weight based on the weight of NVP.

A stabilizer may be directly added to a feed NVP solution or a mother liquor at the inlet of a crystallizer. A specific amount of a stabilizer dissolved or dispersed in feed NVP or a stabilizer present in a crystallization process can inhibit or reduce NVP polymerization and thus can prevent liquid or slurry viscosity from increasing. The slurry discharged from the outlet may be transferred to a subsequent filtration process or further to a crystal purification process.

Because impurities in the above mother liquor get enriched as the operation proceeds, it is sometimes necessary to take at least a part of the mother liquor out of the system. This mother liquor may be discarded, but preferably recovered to reduce a product loss. The above stabilizer can be added when the mother liquor is recovered. The mother liquor to be recovered may be subjected to an additional purification method that specifically includes distillation, filtration, centrifugal separation, adsorption and extraction purification.

A known purification method can be used as the above purification method. Distillation purification includes simple distillation, continuous multistage distillation and batch multistage distillation. Filtration purification includes pressure filtration, vacuum filtration and gravity filtration. Centrifugal separation purification includes decantation and centrifugal filtration. Adsorption purification includes fixed-bed adsorption using an adsorbent such as activated carbon, silica gel, alumina and a molecular sieve, moving-bed adsorption, fluidized-bed adsorption and agitated-tank adsorption. Extraction purification includes batch extraction, multiple extraction, semibatch extraction and multistage extraction.

(iii) Filtration Process

A filtration process is not particularly restricted so long as an obtained crystal phase and a liquid residue phase can be separated. A known continuous or batch filtration method is generally used.

(iv) Crystal Purification Process

A crystal purification (or rectification) process is not restricted and is preferably used when higher-purity of NVP is required. Crystal purification is not particularly restricted, but preferably uses a method that makes use of sweating. Sweating is a method for crystal purification wherein a relatively impure part of crystals is melted away by melting a part of the crystals to purify the crystals, and it is not limited especially. For example, a tower type purification apparatus (KCP made by Kureha Engineering Co. Ltd.), a falling liquid film type apparatus (MWB) and the like are used.

The crystals from the first crystallization process and the second crystallization process are preferably transferred in a crystal form without melting in view of energy efficiency.

The liquid containing impurities generated in these processes can be used after mixed with mother liquors from the second and subsequent crystallization process.

Other embodiments of the present invention will be further described in detail.

The method based on the second embodiment of the present invention is a method for stably producing high-purity NVP and characterized by controlling the water content in a feed NVP solution at the inlet of a crystallizer within a specific range. The above method includes a method having at least one crystallization process where a multistage fractional crystallization process or single or plural dynamic or static crystallization stages are included, and a method where crystal purification is carried out after crystallization. The water content needs to be adjusted at least at the inlet of the first crystallization process, but may be controlled or may not be controlled in the second and subsequent crystallization process depending on circumstances.

Next, feed NVP supplied at the inlet of a crystallizer, a crystallization process, a filtration process and a crystal purification process will be described in order. Since this method can be applied to the first embodiment, the description of the part overlapping with the first embodiment will be omitted. Combination of each process and adjustment of a water content are main differences between two embodiments.

(i') Feed NVP to be Supplied at the Inlet of a Crystallizer

The object material of attention in the second embodiment is water. The water content in a feed NVP solution at the inlet of a crystallizer is preferably not lower than 0.7% by weight and not higher than 10% by weight, more preferably not lower than 0.8% by weight and not higher than 7% by weight and particularly most preferably not lower than 1% by weight and not higher than 5% by weight.

When the water content is lower than 0.7% by weight, crystals of NVP and the like deposit on the heat transfer surface of a crystallizer causing plugging in the crystallizer, which leads to forced suspension of operation. When the water content is more than 10% by weight on the contrary, production rate of NVP is reduced, which is not preferable from the industrial and economical standpoints.

The water content at the inlet of a crystallizer should be controlled so as to be within the above range. The method for controlling the water content is not particularly restricted and includes a method where the water content in crude NVP introduced in an adjusting tank is measured and controlled by adding crude NVP or water based on the measurement, and a method where the water content in crude NVP is measured and controlled by adding crude NVP or water using a device such as a static mixer installed in a pipeline before the inlet of a crystallizer.

The pH value of a feed NVP solution at the inlet of a crystallizer is preferably not lower than 6.0 and not higher than 13.0, more preferably not lower than 6.5 and not higher than 12.5 and particularly most preferably not lower than 7.0 and not higher than 12.0. When the pH value is not within the above range, production rate of NVP is reduced, which is not preferable from the industrial and economical standpoints.

The temperature of a feed NVP solution at the inlet of a crystallizer is not particularly restricted so long as the solution does not freeze, and is preferably not lower than 7.0° C. and not higher than 30.0° C., more preferably not lower than 9.0° C. and not higher than 25.0° C. and particularly most preferably not lower than 11.0° C. and not higher than 20.0° C. When the temperature is too high, much energy is required to crystallize NVP leading to unstable production. Therefore, the temperature is preferably within the above range.

The temperature is measured with a resistance thermometer bulb one minute after the thermometer is set. A thermocouple can be used depending on circumstances.

Next, the present invention will be described in detail based on the attached drawings.

The second embodiment can be applied to the method shown in FIG. 1 described in the first embodiment. In other words, at least two crystallizers are used and distilled NVP is supplied to the first crystallization process, whereas the mixture of NVP recovered from the first crystallization process and NVP recovered from the second crystallization process is supplied to the second crystallization process after the water content thereof is adjusted.

Figure 2:
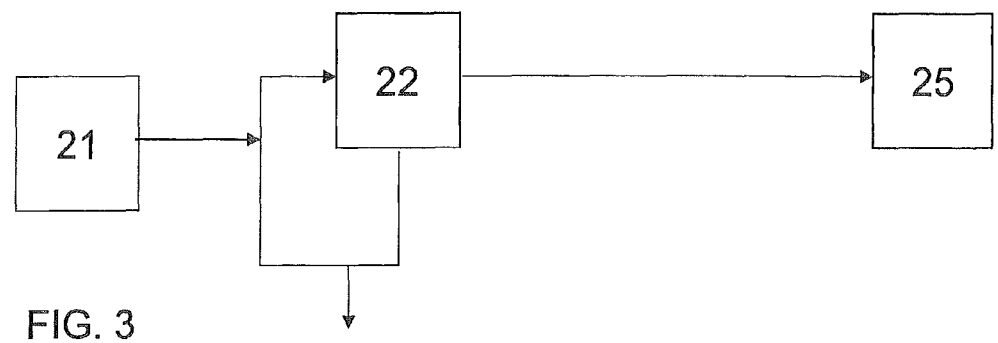
FIG. 2 is an illustration showing another method for purifying NVP in crystallization.

FIG. 2 is an illustration showing another method for purifying NVP in crystallization.

Purification of NVP is carried out using crystallizer 22 in FIG. 2. One crystallizer is used, and distilled NVP and NVP recovered from a crystallization process are mixed and then the water content of the mixture is adjusted. In other words, feed NVP is obtained by mixing distilled NVP 21 and the mother liquor recovered from the crystallization process and then adjusting the water content of the mixed liquid. Feed NVP is purified using crystallizer 22 and then filtered to obtain crystals as product 25.

Part of a mother liquor recovered from a crystallization process is taken out of the system to adjust the concentration of impurities in this method. In other words, the concentration of impurities in a mother liquor is controlled so as to be generally not higher than 10%, preferably not higher than 6%. The case of FIG. 3 is the same in this respect.

Figure 3:
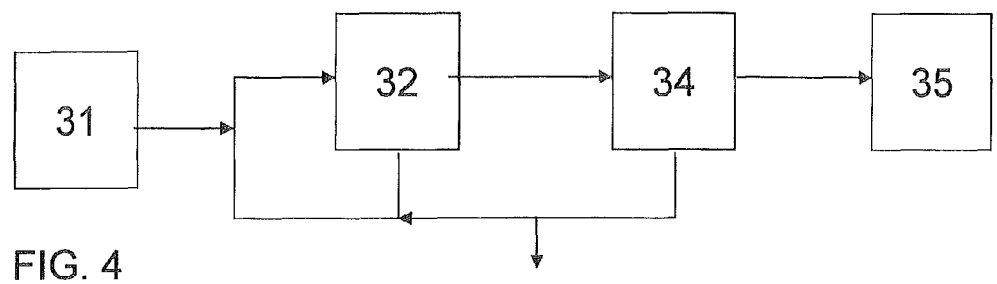
FIG. 3 is an illustration showing the other method for purifying NVP in crystallization.

FIG. 3 is an illustration showing the other method for purifying NVP in crystallization.

In FIG. 3, crystallizer 32 and crystal purification apparatus 34 are combined to carry out NVP purification. NVP of higher purity is obtained by combining a crystallizer with a crystal purification apparatus than that obtained in the case of a crystallizer alone.

One crystallizer and one crystal purification apparatus are used, and distilled NVP and NVP recovered from a crystallization process and, as needed, NVP recovered from a crystal purification process are mixed and then the water content in the mixture is adjusted. In other words, feed NVP is obtained by mixing distilled NVP 31, the mother liquor recovered from the crystallization process using crystallizer 32 and, as needed, the mother liquor and sweating solution recovered from a crystal purification process using crystal purification apparatus 34 and then adjusting the water content in the mixed liquid. Feed NVP is treated in crystallizer 32 and filtered to obtain crude crystals, which are then purified in crystal purification apparatus 34 to obtain product 35.

A part of a mother liquor and sweating solution recovered from a crystal purification process is taken out of the system to adjust the concentration of impurities in this method.

Figure 4:
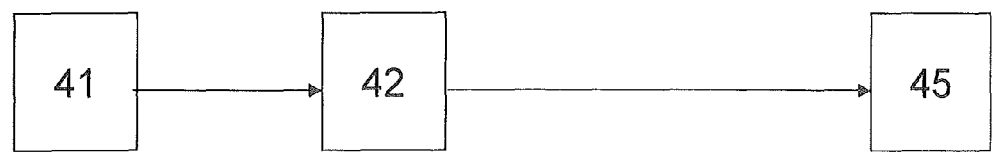
FIG. 4 is an illustration showing still the other method for purifying NVP in crystallization.

FIG. 4 is an illustration showing still the other method for purifying NVP in crystallization.

Distilled NVP 41 is crystallized in a crystallization process using crystallizer 42 to obtain crystals as product 45.

EXAMPLES

Hereinafter, the present invention is described in detail with reference to the examples, however, the present invention is not limited by those examples.

Preparation Method of Feed NVP as a Raw Material for Crystallization

Example I

Feed NVP to be supplied to a crystallization process was obtained by gas-phase dehydration of N-hydroxyethyl-2-pirrolidone followed by purification by distillation. The obtained crude NVP had a purity of 97.3125% and an organic-impurity concentration of 21,600 ppm. The organic impurities include 2-pirrolidone which is a decomposition product of N-hydroxyethyl-2-pirrolidone, N-hydroxyethyl-2-pirrolidone which is an unreacted raw material, polymers and the like.

Example II

Feed NVP to be supplied to a crystallization process was obtained by gas-phase dehydration of N-hydroxyethyl-2-pirrolidone followed by purification by distillation. The purity and the water content of the distilled NVP were in the range of 98.85% to 98.40% and in the range of 0.02% to 0.03% respectively.

NVP concentration, water content and pH of feed NVP and NVP in examples were measured by gas chromatography, Karl Fischer Method and a pH meter respectively.

Measurement Method of NVP Concentration by Gas Chromatography

NVP concentration (sometimes referred to as purity) is measured using gas chromatography (column: DB-1 made by SPELCO, carrier gas: He, flow rate: 17.2 mL/min, temperature: 60° C. to 250° C.).

Measurement Method of Water Content by Karl Fischer Method

Water content is measured using a Karl Fischer meter (DL18 model made by METTLER, solvent: methanol).

Measurement Method of pH 45 g of pure water in which the pH is adjusted to be 6 to 7 is mixed with 5 g of the sample in a 50 mL screw tube to prepare an aqueous solution of 10% by weight of the composition. The aqueous solution is set in a pH meter within one minute and then the pH value is measured after agitation at 25° C. for one minute followed by two minute standing.

pH meter (F-12 model made by HORIBA Ltd., electrode: #6366-10D)

Example I-1

Crude NVP was supplied continuously to horizontal multistage cooling crystallizer 1 (the first crystallization process) to obtain a Slurry containing NVP crystals and a mother liquor. The above crystallizer was operated under the conditions of a feed rate of the crude NVP solution to above crystallizer 1 of 75 kg/h, a feed temperature of 6.5° C. and a retention time of 4 hours.

The obtained slurry was filtered with a belt-type filter. The obtained NVP crystals had a purity of 99.1975% and an organic-impurity concentration of 5,150 ppm. The rate of NVP crystal generation was 15 kg/h.

The crystals obtained by filtration were mixed with the crystals from the second crystallization process to be described later and then supplied continuously to a tower type purification apparatus at a feed rate of 50 kg/h. Ultrapure NVP was obtained at a rate of 35 kg/h under the conditions of a retention time of 0.5 hours and heating at the top of the tower with hot water of 30° C. to 50° C. Analysis of the obtained NVP showed a purity of 99.9920% and an organic-impurity concentration of 50 ppm.

The mother liquor after filtration with a belt-type filter from the first crystallization process was mixed with the mother liquor from the second crystallization process and then supplied continuously to another horizontal multistage cooling crystallizer 2 (the second crystallization process) to obtain a slurry containing NVP crystals and a mother liquor. The above crystallizer was operated under the conditions of a flow rate of the mother liquor to crystallizer 2 of 85 kg/h, a feed temperature of 6.5° C. and a retention time of 2.5 hours. The obtained NVP crystals had a purity of 98.9930% and an organic-impurity concentration of 7,700 ppm. The rate of NVP crystallization was 35 kg/h.

The mother liquor obtained by filtrating the slurry from above crystallizer 2 with a belt-type filter was sent back to above crystallizer 2 at a rate of 25 kg/h.

Example I-2

Crude NVP was supplied continuously to a drum flaker (the first crystallization process) to obtain NVP crystals and a mother liquor. The drum flaker was operated under the conditions of a feed rate of the crude NVP solution to the drum flaker of 75 kg/h, a feed temperature of 6.5° C., a drum surface area of 2 $m^2$ and a retention time of 2 hours. The obtained NVP crystals had a purity of 99.0995% and an organic-impurity concentration of 6,300 ppm. The rate of NVP crystallization was 7.5 kg/h.

The above crystals were mixed with the crystals from the second crystallization process to be described later and then supplied continuously to a tower type purification apparatus at a feed rate of 50 kg/h. Ultrapure NVP was obtained at a rate of 35 kg/h under the conditions of a retention time of 0.5 hours and heating at the top of the tower with hot water of 30° C. to 50° C. Analysis of the obtained NVP showed a purity of 99.9910% and an organic-impurity concentration of 50 ppm.

The mother liquor from the drum flaker was mixed with the mother liquor sent back from the second crystallization process and then supplied continuously to a horizontal multistage cooling crystallizer (the second crystallization process) to obtain a slurry containing NVP crystals and a mother liquor. The above crystallizer was operated under the conditions of a feed rate of the mother liquor to the crystallizer of 102 kg/h, a feed temperature of 6.5° C. and a retention time of 3 hours. The obtained NVP crystals had a purity of 98.9475% and an organic-impurity concentration of 8,400 ppm. The rate of NVP crystallization was 42.5 kg/h.

The mother liquor obtained by filtrating the slurry from above crystallizer 2 with a belt-type filter was sent back to above crystallizer 2 at a rate of 35 kg/h.

Example I-3

Crude NVP was supplied continuously to horizontal multistage cooling crystallizer 1 (the first crystallization process) to obtain a slurry containing NVP crystals and a mother liquor. The above crystallizer was operated under the conditions of a feed rate of the crude NVP solution to above crystallizer 1 of 75 kg/h, a feed temperature of 6.5° C. and a retention time of 4 hours. The obtained slurry was filtered with a belt-type filter. The obtained NVP crystals had a purity of 98.9995% and an organic-impurity concentration of 6,500 ppm. The rate of NVP crystallization was 15 kg/h.

The mother liquor after filtration with a belt-type filter was mixed with the mother liquor sent back from the second crystallization process and then supplied continuously to horizontal multistage cooling crystallizer 2 (the second crystallization process) to obtain a slurry containing NVP crystals and a mother liquor. The above crystallizer was operated under the conditions of a feed rate of the mother liquor to the crystallizer of 85 kg/h, a feed temperature of 6.5° C. and a retention time of 2 hours. The obtained NVP crystals had a purity of 98.9040% and an organic-impurity concentration of 7,500 ppm. The rate of NVP crystallization was 35 kg/h.

The mother liquor after filtration was sent back to the second crystallization process at a rate of 25 kg/h, whereas the crystals after filtration were supplied to a tower type purification apparatus at a rate of 35 kg/h. Ultrapure NVP was obtained at a rate of 25 kg/h under the conditions of a retention time of 0.5 hours and heating at the top of the tower with hot water of 30° C. to 50° C. Analysis of the obtained NVP showed a purity of 99.9885% and an organic-impurity concentration of 70 ppm.

Example I-4

Crude NVP was supplied continuously to a tank type crystallizer (the first crystallization process) to obtain a slurry containing NVP crystals and a mother liquor. The tank type crystallizer was operated under the conditions of a feed rate of the crude NVP solution to the crystallizer of 75 kg/h, a feed temperature of 6.5° C. and a retention time of 4 hours. The obtained slurry was then separated into crystals and a mother liquor with a centrifugal separator. The obtained NVP crystals had a purity of 99.1755% and an organic-impurity concentration of 5,500 ppm. The rate of NVP crystallization was 15 kg/h.

The separated mother liquor was mixed with the mother liquor sent back from the second crystallization process and then supplied continuously to a horizontal multistage cooling crystallizer (the second crystallization process) to obtain a slurry containing NVP crystals and a mother liquor. The crystallizer was operated under the conditions of a feed rate of the mother liquor to the crystallizer of 85 kg/h, a feed temperature of 6.5° C. and a retention time of 2 hours. The obtained NVP crystals had a purity of 98.194% and an organic-impurity concentration of 7,500 ppm. The rate of NVP crystallization was 35 kg/h.

The mother liquor obtained by filtrating the slurry from the second crystallization process with a belt-type filter was sent back to the second crystallization process at a rate of 25 kg/h.

The crystals after filtration were mixed with the crystals from the first crystallization process and then supplied continuously to a tower type purification apparatus at a rate of 50 kg/h. Ultrapure NVP was obtained at a rate of 35 kg/h under the conditions of a retention time of 0.5 hours and heating at the top of the tower with hot water of 30° C. to 50° C. Analysis of the obtained NVP crystals showed a purity of 99.9765% and an organic-impurity concentration of 70 ppm.

Comparative Example I-1

Crude NVP was supplied continuously to a horizontal multistage cooling crystallizer (the first crystallization process) to obtain a slurry containing NVP crystals and a mother liquor. The feed rate of the mother liquor to the above crystallizer was 75 kg/h, which consisted of 10 kg/h of virgin crude NVP and 65 kg/h of the recovered mother liquor from the first crystallization process. This mixed liquid was supplied at a temperature of 6.5° C. and a retention time of 4 hours. The rate of NVP crystallization was 15 kg/h.

The above slurry was then taken out of the first crystallization process and filtered with a belt-type filter. The obtained NVP had a purity of 97.3985% and an organic-impurity concentration of 15,450 ppm.

The crystals after filtration was supplied continuously to a tower type purification apparatus at a retention time of 1 hour to obtain high-purity NVP at a rate of 10.5 kg/h. The NVP had a purity of 98.6795% and an organic-impurity concentration of 8,350 ppm.

Comparative Example I-2

Two parallel-arranged horizontal multistage cooling crystallizers were referred each to as the first crystallization process and the second crystallization process. Crude NVP was supplied continuously to each crystallization process to obtain a slurry containing NVP crystals and a mother liquor. The feed rate of the mother liquor to each crystallization process was 37.5 kg/h, which consisted of 5 kg/h of virgin crude NVP and 32.5 kg/h of the recovered mother liquor from each crystallization process. This mixed liquid was supplied at a temperature of 6.5° C. and a retention time of 6 hours. The rate of NVP crystallization was 15 kg/h in each process.

The above slurry was then taken out of each crystallization process and filtered with a belt-type filter. The NVP obtained from the first crystallization process had a purity of 97.1825% and an organic-impurity concentration of 16,850 ppm, whereas the NVP obtained from the second crystallization process had a 97.2225% and an organic-impurity concentration of 16,550 ppm.

The crystals from each crystallization process were mixed after filtration and supplied continuously to a tower type purification apparatus at a retention time of 1 hour to obtain NVP at a rate of 10.5 kg/h. The NVP had a purity of 98.3465% and an organic-impurity concentration of 9,650 ppm.

The results of Examples 1 to 4 and Comparative Examples 1 to 2 are shown in Table I-1.

TABLE I-1

| | First Crystal Process | Second Crystal Process | Purification Process | | |
|---|---|---|---|---|---|
| | NVP Purity (%) | NVP Purity (%) | Retention Time (h) | Rate of Crystal (kg/h) | NVP Purity (%) |
| Example I-1 | 99.1975 | 98.9930 | 0.5 | 35 | 99.9920 |
| Example I-2 | 99.0995 | 98.9475 | 0.5 | 35 | 99.9910 |
| Example I-3 | 98.9995 | 98.9040 | 0.5 | 25 | 99.9885 |
| Example I-4 | 98.1755 | 98.1940 | 0.5 | 35 | 99.9765 |
| Com. Exam. I-1 | 97.3985 | — | 1 | 10.5 | 98.6795 |
| Com. Exam. I-2 | 97.1825 | 97.2225 | 1 | 10.5 | 98.3465 |

Crystal: Crystallization
Com. Exam.: Comparative Example

The NVP obtained from the first crystallization process of each example had generally higher purity than that obtained from the first crystallization process of each comparative example. Similarly, the NVP obtained from the second crystallization process of each example had higher purity than that obtained from the second crystallization process of Comparative Example 2. Therefore, the effect of the present invention that high-purity NVP could be obtained by supplying the mother liquor from the first crystallization process to the second crystallization process was demonstrated.

Further, NVP of higher purity from each crystallization process improved efficiency of a purification process where a sweating phenomenon was applied. As apparent from Table I-1, it can be understood that NVP of higher purity is obtained in each example than in each comparative example at a rate of crystallization as high or twice as high as that in each comparative example even though the retention time in each example is only half of that in each comparative example. High-purity NVP can be efficiently produced by supplying the mother liquor from the first crystallization process to the second crystallization process.

Example II-1

NVP was purified according to the method shown in FIG. 4.

Distilled NVP of a water content of 0.02% by weight and a purity of 98.80% was added with water to obtain feed NVP (pH: 11.0, temperature: 11.3° C.) of a water content of 1.18% by weight, which was supplied continuously at a feed rate of 75 kg/h to a horizontal multistage cooling crystallizer and crystallized for purification at 6.5° C. and a retention time of 4 hours for 7 days in series. It turned out that NVP of a purity of not lower than 99.98% was stably obtained in a continuous operation without depositing of crystals on the heat transfer surface of the crystallizer that may cause a shutdown of the crystallizer.

Example II-2

NVP was purified according to the method shown in FIG. 2.

Crystallization was carried out in the same way as Example II-1 except that distilled NVP of a water content of 0.02% by weight and a purity of 99.12% was mixed with the NVP of a water content of 2.20% by weight and a purity of 98.54% recovered from a crystallizer at a mixing ratio of 4:6 by weight and then added with water to obtain feed NVP (pH: 11.3, temperature: 13.2° C.) of a water content of 3.57% by weight. It turned out that NVP of a purity of not lower than 99.97% was stably obtained in a continuous operation without depositing of crystals on the heat transfer surface of the crystallizer that may cause a shutdown of the crystallizer.

Example II-3

NVP was purified according to the method shown in FIG. 2.

Crystallization was carried out in the same way as Example II-1 except that distilled NVP of a water content of 0.03% by weight and a purity of 99.24% was mixed with the NVP of a water content of 1.80% by weight and a purity of 98.33% recovered from a crystallization mother liquor at a mixing ratio of 4:6 by weight and then added with water to obtain feed NVP (pH: 11.0, temperature: 10.1° C.) of a water content of 8.89% by weight. The crystallization mother liquor was taken out of the system at a rate of 2 L/h to prevent quality deterioration of the NVP, whereas water was added to the system at a rate of 0.2 L/h to keep the water content constant. It turned out that NVP of a purity of not lower than 99.95% was stably obtained in a continuous operation without depositing of crystals on the heat transfer surface of the crystallizer that may cause a shutdown of the crystallizer.

Example II-4

NVP was purified according to the method shown in FIG. 3.

Distilled NVP of a water content of 0.03% by weight and a purity of 98.99% was mixed with the NVP of a water content of 1.15% by weight and a purity of 98.08% recovered from a crystallization mother liquor at a mixing ratio of 4:6 by weight and then added with water to obtain feed NVP (pH: 10.8, temperature: 12.2° C.) of a water content of 0.91% by weight, which was supplied continuously at a feed rate of 75 kg/h to a horizontal multistage cooling crystallizer and crystallized for purification at a temperature of 6.5° C. and a retention time of 4 hours for 7 days in series. The crystallization mother liquor was taken out of the system at a rate of 4 L/h to prevent quality deterioration of the NVP, whereas water of 0.4 L was added to the system every 8 hours to keep the water content constant. It turned out that NVP of a purity of not lower than 99.95% was stably obtained in a continuous operation without depositing of crystals on the heat transfer surface of the crystallizer that may cause a shutdown of the crystallizer. The obtained NVP was supplied to a tower type purification apparatus where a sweating phenomenon was applied and subjected to further purification there to obtain NVP of a purity of not lower than 99.99%.

Comparative Example II-1

NVP was purified according to the method shown in FIG. 2.

Crystallization was carried out in the same way as Example II-1 except that distilled NVP of a water content of 0.02% by weight and a purity of 97.87% was mixed with the NVP of a water content of 0.56% by weight and a purity of 98.33% recovered from a crystallization mother liquor at a mixing ratio of 4:6 by weight to obtain the feed NVP (pH: 10.3, temperature: 11.9° C.), which was not added with water. It turned out that after 5 hours since beginning of the operation, crystals began to deposit on the heat transfer surface of the crystallizer with the production rate decreasing gradually and after 23 hours the operation was forced to stop.

Comparative Example II-2

NVP was purified according to the method shown in FIG. 2.

Crystallization was carried out in the same way as Example II-1 except that distilled NVP of a water content of 0.03% by weight and a purity of 99.43% was mixed with the NVP of a water content of 0.69% by weight and a purity of 98.33% recovered from a crystallization mother liquor at a mixing ratio of 4:6 by weight to obtain feed NVP (pH: 10.3, temperature: 6.5° C.). The crystallization mother liquor was taken out of the system at a rate of 4 L/h to prevent quality deterioration of the NVP, but water was not added. It turned out that after 3 hours since beginning of the operation, crystals began to deposit on the heat transfer surface of the crystallizer with the production rate decreasing gradually and after 11 hours the operation was forced to stop.

Example II-5

NVP was purified according to the method shown in FIG. 2.

Distilled NVP of a water content of 0.02% was mixed with the mother liquor of a water content of 0.47% recovered from a horizontal multistage cooling crystallizer at a mixing ratio of about 1:6 (by weight) and then added with water to obtain feed NVP adjusted to be of a water content of 1.75% by weight, a pH of 11.7 and a temperature of 13.0° C., which was continuously supplied to the crystallizer.

Crystallization was carried out under the conditions of a feed rate of 75 kg/h, a slurry concentration of 20%, a temperature of 7.0° C. and a retention time of 4 hours.

After 7 days in series, NVP of a purity of not lower than 99.98% could be stably obtained without depositing of crystals on the heat transfer surface of the crystallizer.

The above descriptions are on preferable embodiments of the present invention, and it should be understood that various alterations and modifications are made within the scope of the present invention without departing from the spirit and scope of the present invention.

The invention claimed is:

1. A method for producing N-vinyl-2-pyrrolidone by crystallization comprising:
   controlling a water content in a feed N-vinyl-2-pyrrolidone solution at an inlet of a crystallizer so as to be not lower than 0.7% by weight and not higher than 10% by weight based on the total weight of the N-vinyl-2-pyrrolidone solution;
   adjusting the pH value of the feed N-vinyl-2-pyrrolidone solution before supplying to a crystallization process to be within the range of from 10.8 to 12.0; and
   supplying the resulting pH-adjusted feed N-vinyl-2-pyrrolidone solution to the crystallization process,
   wherein a temperature of the feed N-vinyl-2-pyrrolidone solution before supplying to the crystallization process is within the range of from 9.0° C. to 25.0° C.,
   wherein the N-vinyl-2-pyrrolidone solution resulting from the method has a purity of more than 99%.

2. The method according to claim 1, wherein the pH value of the feed N-vinyl-2-pyrrolidone solution before supplying to the crystallization process is within the range of from 11.3 to 12.0.

3. The method according to claim 1, wherein the pH value of the feed N-vinyl-2-pyrrolidone solution before supplying to the crystallization process is within the range of from 11.3 to 12.0.

4. The method according to claim 1, wherein the N-vinyl-2-pyrrolidone solution resulting from the method has a purity of at least 99.9765%.

5. The method according to claim 1, wherein the feed N-vinyl-2-pyrrolidone contains at least one selected from the group consisting of distilled N-vinyl-2-pyrrolidone and N-vinyl-2-pyrrolidone recovered from a purification process.

6. The method according to claim 1, wherein the water content is within the range of not lower than 0.8% by weight and not higher than 7% by weight, based on the total weight of the N-vinyl-2-pyrrolidone solution.

7. The method according to claim 1, wherein the temperature of the feed N-vinyl-2-pyrrolidone solution before supplying to the crystallization process is within the range of from 11.0° C. to 20.0° C.

8. The method according to claim 1, wherein a part of a mother liquor recovered from the crystallization process is subjected to purification to adjust the concentration of impurities in the recovered mother liquor.

9. The method according to claim 1, wherein the crystallization process is a first crystallization process conducted in a first crystallizer, the method further comprising:
   conducting a second crystallization process conducted in a second crystallizer,
   supplying crystals obtained from the first crystallization process to a crystal purification process where a sweating phenomenon is applied,
   mixing (1) a mother liquor obtained from the first crystallization process, (2) a mother liquor obtained from the second crystallization process, and (3) a mother liquor and a sweating solution obtained from the crystal purification process, to obtain a feed solution for the second crystallization process, and
   supplying the feed solution to the second crystallization process.

10. The method according to claim 1, further comprising:
    supplying crystals obtained from the crystallization process to a crystal purification process where a sweating phenomenon is applied,
    mixing (1) a mother liquor obtained from the crystallization process and (2) a part of a mother liquor and a sweating solution obtained from the crystal purification process, to obtain a feed solution for the crystallization process,
    introducing the feed solution to the crystallization process, and
    adjusting a concentration of impurities of the feed solution by not adding a part of the mother liquor and the sweating solution obtained from the crystal purification process to the feed solution.

11. The method according to claim 1, further comprising adding a stabilizer to the feed N-vinyl-2-pyrrolidone solution, wherein the stabilizer comprises N,N'-di-sec-butyl-p-phenylenediamine, p-phenylenediamine, N,N'-diethyl-p-phenylenediamine, N,N'-diphenyl-p-phenylenediamine, 2,6-t-butyl-4-hydroxytoluene, or a combination thereof.

* * * * *